(12) United States Patent
    Itkowitz et al.

(10) Patent No.:    US 12,697,179 B2
(45) Date of Patent:      Aug. 4, 2026

(54) SYSTEMS AND METHODS FOR ONSCREEN MENUS IN A TELEOPERATIONAL MEDICAL SYSTEM

(71) Applicant: INTUITIVE SURGICAL OPERATIONS, INC., Sunnyvale, CA (US)

(72) Inventors: Brandon D. Itkowitz, San Jose, CA (US); Julie L. Berry, San Jose, CA (US); Anthony M. Jarc, Johns Creek, GA (US); Amy E. Kerdok, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 53 days.

(21) Appl. No.: 18/336,875

(22) Filed: Jun. 16, 2023

(65)          Prior Publication Data

US 2023/0389999 A1     Dec. 7, 2023

Related U.S. Application Data

(63) Continuation of application No. 16/324,891, filed as application No. PCT/US2017/046446 on Aug. 11, 2017, now Pat. No. 11,730,550.
(Continued)

(51) Int. Cl.
    *G16H 40/60*      (2018.01)
    *A61B 34/00*      (2016.01)
    (Continued)

(52) U.S. Cl.
    CPC .............. *A61B 34/25* (2016.02); *A61G 13/02* (2013.01); *G16H 40/63* (2018.01);
    (Continued)

(58) Field of Classification Search
None
See application file for complete search history.

(56)           References Cited

U.S. PATENT DOCUMENTS

| | | | |
|---|---|---|---|
| 6,129,671 A | 10/2000 | Hastings | |
| 7,439,956 B1 * | 10/2008 | Albouyeh | ............. G06F 3/0208 |
| | | | 361/679.09 |

(Continued)

FOREIGN PATENT DOCUMENTS

| | | |
|---|---|---|
| DE | 102008043531 A1 | 5/2010 |
| JP | 2009502337 A | 1/2009 |

(Continued)

OTHER PUBLICATIONS

Extended European Search Report for Application No. 17840324.2, mailed on Feb. 28, 2020, 7 pages.

(Continued)

*Primary Examiner* — Robert A Sorey
(74) *Attorney, Agent, or Firm* — Haynes & Boone, LLP.

(57)          ABSTRACT

A system comprises a teleoperational assembly including an operator input system and a teleoperational manipulator configured for operation by the operator input system. The teleoperational manipulator is coupled to a medical instrument in a surgical environment. The system also comprises a processing unit including one or more processors. The processing unit is configured to retrieve a user profile for a user, the user profile including a parameter established during a prior teleoperational procedure. The parameter includes an ergonomic setup for an input device of the operator input system. The input device is configured to operate the teleoperational manipulator. The processing unit is also configured to provide instructions to configure an operation of the teleoperational assembly based upon the parameter. The operation includes adjusting the operator (Continued)

input system based on the at least one of the ergonomic setup for the operator input system.

20 Claims, 5 Drawing Sheets

Related U.S. Application Data

(60) Provisional application No. 62/374,254, filed on Aug. 12, 2016.

(51) Int. Cl.
| | | |
|---|---|---|
| *A61G 13/02* | (2006.01) | |
| *G16H 40/63* | (2018.01) | |
| *A61B 34/35* | (2016.01) | |

(52) U.S. Cl.
CPC ... *A61B 2034/252* (2016.02); *A61B 2034/256* (2016.02); *A61B 2034/258* (2016.02); *A61B 34/35* (2016.02)

(56) References Cited

U.S. PATENT DOCUMENTS

| | | | |
|---|---|---|---|
| 8,120,301 B2 | 2/2012 | Goldberg et al. | |
| 9,190,062 B2 | 11/2015 | Haughay et al. | |
| 9,203,814 B2 | 12/2015 | Perez et al. | |
| 2004/0010328 A1* | 1/2004 | Carson .................. | G06Q 10/00 |
| | | | 707/999.107 |
| 2004/0143905 A1* | 7/2004 | Pastyr .................. | A61B 6/0407 |
| | | | 5/81.1 R |
| 2007/0027459 A1* | 2/2007 | Horvath ................ | A61B 90/98 |
| | | | 606/147 |
| 2008/0312953 A1 | 12/2008 | Claus | |
| 2008/0314973 A1* | 12/2008 | Zuhars ................. | G16H 40/40 |
| | | | 705/2 |

| | | | |
|---|---|---|---|
| 2009/0103785 A1* | 4/2009 | Pedroza | |
| 2010/0051386 A1* | 3/2010 | Machovic Basic .... | A61B 90/60 |
| | | | 182/148 |
| 2010/0217991 A1* | 8/2010 | Choi ...................... | G16H 20/40 |
| | | | 380/255 |
| 2013/0185088 A1 | 7/2013 | Bryant | |
| 2015/0169857 A1 | 6/2015 | Wang et al. | |
| 2016/0170402 A1* | 6/2016 | Lindström ............... | A47B 9/00 |
| | | | 700/275 |
| 2017/0020627 A1* | 1/2017 | Tesar ................... | A61B 90/361 |
| 2017/0143429 A1* | 5/2017 | Richmond ............. | A61B 34/37 |
| 2017/0209639 A1* | 7/2017 | Wolter ................ | A61M 3/0258 |
| 2018/0085276 A1* | 3/2018 | Brodard ............... | A61N 1/0452 |
| 2020/0012116 A1* | 1/2020 | Fuerst ................ | G02B 27/0093 |
| 2020/0078105 A1 | 3/2020 | Itkowitz et al. | |
| 2021/0236233 A1* | 8/2021 | Fuerst ................... | G16H 20/40 |

FOREIGN PATENT DOCUMENTS

| | | |
|---|---|---|
| WO | WO-2007016101 A1 | 2/2007 |
| WO | WO-2009052312 A1 | 4/2009 |
| WO | WO-2011060054 A2 | 5/2011 |
| WO | WO-2015142933 A1 | 9/2015 |
| WO | WO-2015142956 A1 | 9/2015 |
| WO | WO-2015143067 A1 | 9/2015 |

OTHER PUBLICATIONS

International Preliminary Report on Patentability for Application No. PCT/US2017/046446, mailed on Feb. 12, 2019, 9 pages (ISRG07840/PCT).

International Search Report and Written Opinion for Application No. PCT/US2017/046446, mailed on Nov. 20, 2017, 12 pages (ISRG07840/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR ONSCREEN MENUS IN A TELEOPERATIONAL MEDICAL SYSTEM

RELATED APPLICATIONS

This patent application is a continuation of U.S. patent application Ser. No. 16/324,891 filed Feb. 11, 2019, which is the U.S. national phase of International Application No. PCT/US2017/046446, filed Aug. 11, 2017, which designated the U.S. and claims priority to and the benefit of the filing date of U.S. Provisional Patent Application 62/374,254, entitled "SYSTEMS AND METHODS FOR ONSCREEN MENUS IN A TELEOPERATIONAL MEDICAL SYSTEM," filed Aug. 12, 2016, all of which are incorporated by reference herein in their entirety.

FIELD

The present disclosure is directed to systems and methods for performing a teleoperational medical procedure and more particularly to systems and methods for providing personalized user configurations.

BACKGROUND

Minimally invasive medical techniques are intended to reduce the amount of tissue that is damaged during invasive medical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments. Imaging instruments provide a user with a field of view within the patient anatomy. Some minimally invasive medical tools and imaging instruments may be teleoperated or otherwise computer-assisted. As teleoperational medical systems and teleoperated medical procedures become increasingly complex, more efficient and personalized systems and methods for configuring the teleoperational medical systems and procedures are needed.

SUMMARY

The embodiments of the invention are summarized by the claims that follow below.

In one embodiment, a system comprises a teleoperational assembly including an operator control system and a teleoperational manipulator configured for operation by the operator control system. The teleoperational manipulator is coupled to a medical instrument in a surgical environment. The system also comprises a processing unit including one or more processors. The processing unit is configured to retrieve a user profile for a user. The user profile including a parameter established during a prior teleoperational procedure. The processing unit is also configured to provide instructions to configure an operation of the teleoperational assembly based upon the parameter.

In another embodiment, a system comprises a teleoperational assembly including an operator control system and a teleoperational manipulator configured for operation by the operator control system. The teleoperational manipulator is coupled to a medical instrument in a surgical environment. The system also includes a processing unit including one or more processors. The processing unit is configured to retrieve a user profile for a user, that includes a parameter established by an operator input. The processing unit is also configured to provide instructions to configure an operation of the teleoperational assembly based upon the parameter.

In another embodiment, a method comprises determining an identity of a user at an operator control system of a teleoperational assembly. The teleoperational assembly includes a teleoperational manipulator configured for teleoperation by the operator control system. The method also includes retrieving a user profile for the user. The user profile includes a first parameter established during a prior teleoperational procedure. The method also includes configuring an operation of a teleoperational assembly, based on the first parameter, during a current teleoperational procedure.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
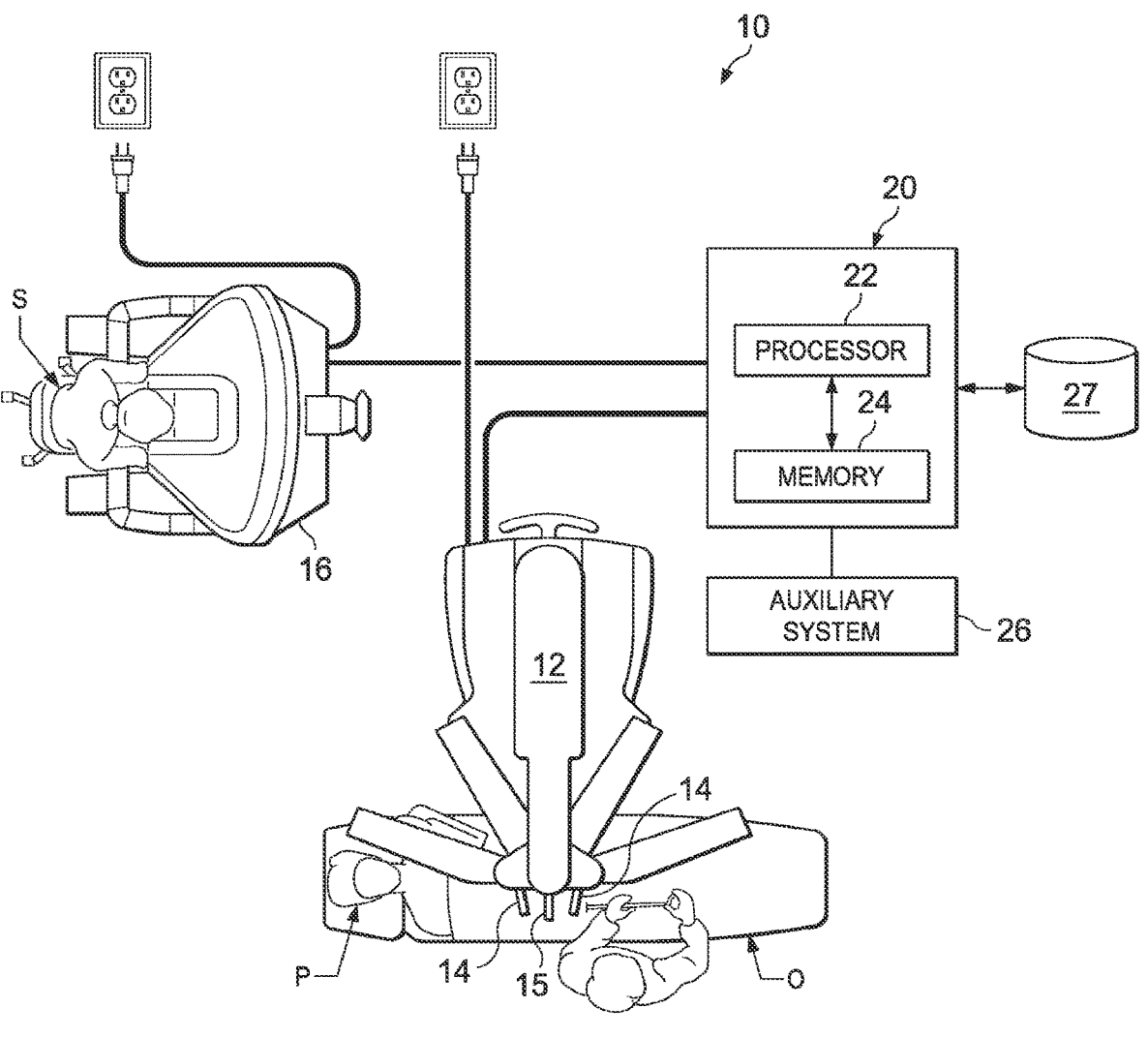
FIG. 1A is a schematic view of a teleoperational medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperational medical system 10 generally includes a teleoperational assembly 12 mounted to or near an operating table O on which a patient P is positioned. The teleoperational assembly 12 may be referred to as a patient side cart when configured as part or all of a cart or when capable of being placed in a cart. A medical instrument system 14 and an endoscopic imaging system 15 are operably coupled to the teleoperational assembly 12. An operator input system 16 allows a surgeon or other type of clinician S to view images of or representing the surgical site and to control the operation of the medical instrument system 14 and/or the endoscopic imaging system 15. The operator input system 16 may also be referred to as a control console 16. In various embodiments, the operator input system 16 may be adaptable for use with one of a plurality of types of teleoperational systems, including, for example multi-port and single port teleoperational platforms.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaw end effectors, applying an electrical potential to an electrode, delivering a medicinal treatment, and the like).

The teleoperational assembly 12 supports and manipulates the medical instrument system 14 while the surgeon S views the surgical site through the console 16. An image of the surgical site can be obtained by the endoscopic imaging system 15, such as a stereoscopic endoscope, which can be manipulated by the teleoperational assembly 12 to orient the endoscopic imaging system 15. An electronics cart 18 can be used to process the images of the surgical site for subsequent display to the surgeon S through the console 16. The number of medical instrument systems 14 used at one time will generally depend on the diagnostic or surgical procedure and the space constraints within the operating room among other factors. The teleoperational assembly 12 may include a kinematic structure of one or more non-servo controlled links (e.g., one or more links that may be manually positioned and locked in place, generally referred to as a set-up structure) and a teleoperational manipulator. The teleoperational assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Instruments 14 may include end effectors having a single working member such as a scalpel, a blunt blade, an optical fiber, or an electrode. Other end effectors may include, for example, forceps, graspers, scissors, or clip appliers.

The teleoperational medical system 10 also includes a control system 20. The control system 20 includes at least one memory 24 and at least one processor 22, and typically a plurality of processors, for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

The control system 20 is in communication with a profile database 27 which stores one or more user profiles. The profile database 27 may be stored in the memory 24 of the teleoperational system. Additionally or alternatively, the profile database 27 may be stored on a device such as a server or a portable storage device that is accessible by the control system via an internal network (e.g., a secured network of a medical facility or a teleoperational system provider) or an external network (e.g., the Internet). The profile database 27 may be distributed throughout two or more locations. For example, the database 27 may be present on multiple devices which may include the devices of different entities and/or a cloud server. Additionally or alternatively, the profile database 27 may be stored on a portable user-assigned device such as a computer, a mobile device, a smart phone, a laptop, an electronic badge, a tablet, a pager, and other similar user devices.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperational assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The control system 20 can be coupled with the endoscopic imaging system 15 and can include a processor to process captured images for subsequent display, such as to a surgeon on the surgeon's console, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated, or they may be positioned in separate locations.

Multiple operator input systems allow more than one operator to control one or more manipulator assemblies in various combinations.

Figure 1B:
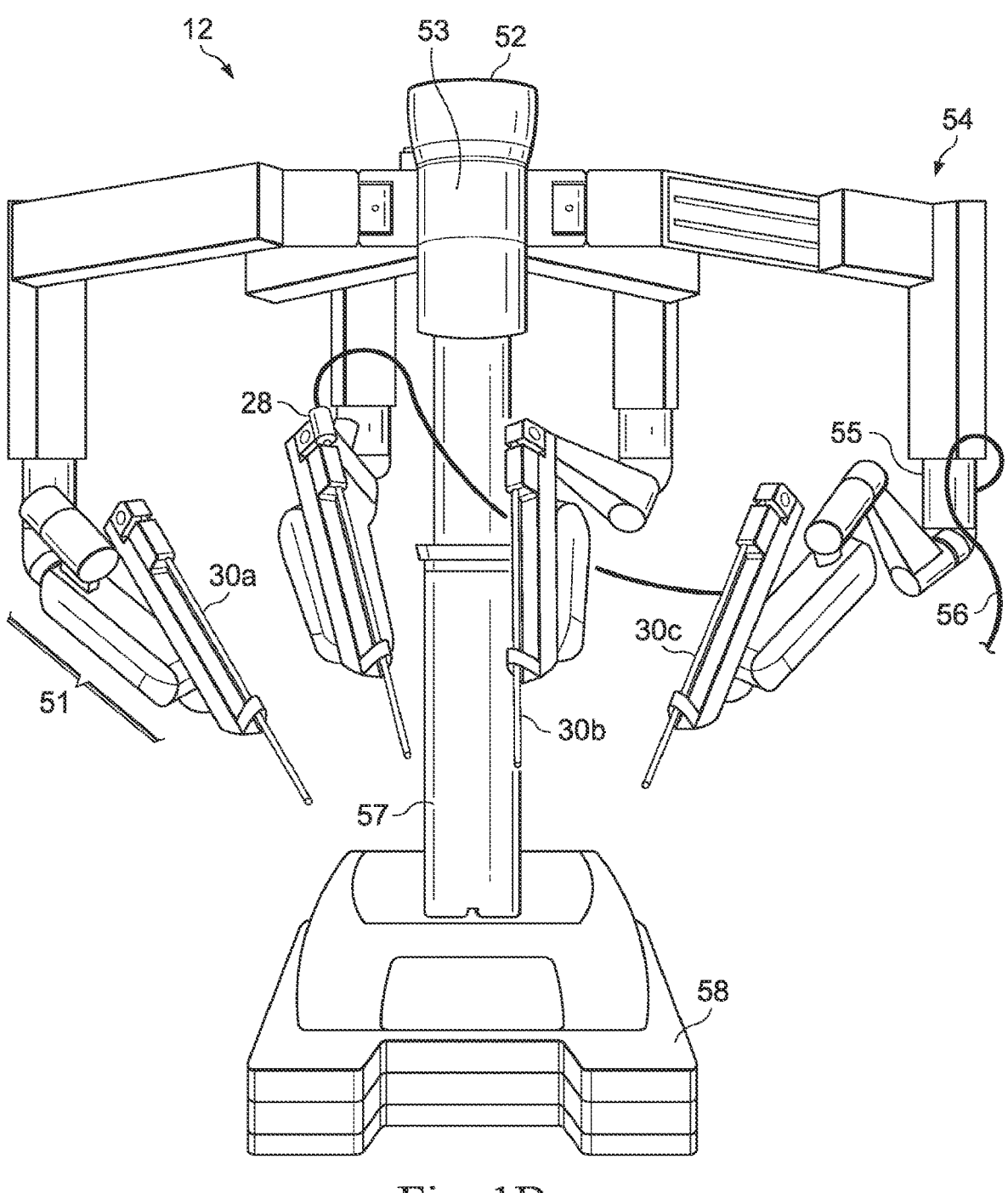
FIG. 1B is a perspective view of a patient side cart, according to one example of principles described herein.

FIG. 1B is a perspective view of one embodiment of a teleoperational assembly 12 which may be referred to as a patient side cart when configured as part or all of a cart or when capable of being placed in a cart. The teleoperational assembly 12 shown provides for the manipulation of three surgical tools 30*a*, 30*b*, 30*c* (e.g., instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30*a-c* can be positioned and manipulated through incisions in the patient so that a kinematic remote center is maintained at the incision to minimize the size of the incision. Images of the surgical site can include images of the distal ends of the surgical tools 30*a-c* when they are positioned within the field-of-view of the imaging device 28.

The teleoperational assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperational assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument such as a surgical tool (e.g. 30*a-c*). The manipulator arms 51 may be teleoperatable. In some examples, the arms 54 connecting to the orienting platform are not teleoperatable. Rather, such arms 54 are positioned as desired before the surgeon S begins operation with the teleoperative components.

Endoscopic imaging systems (e.g., system 15 and device 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

Figure 1C:
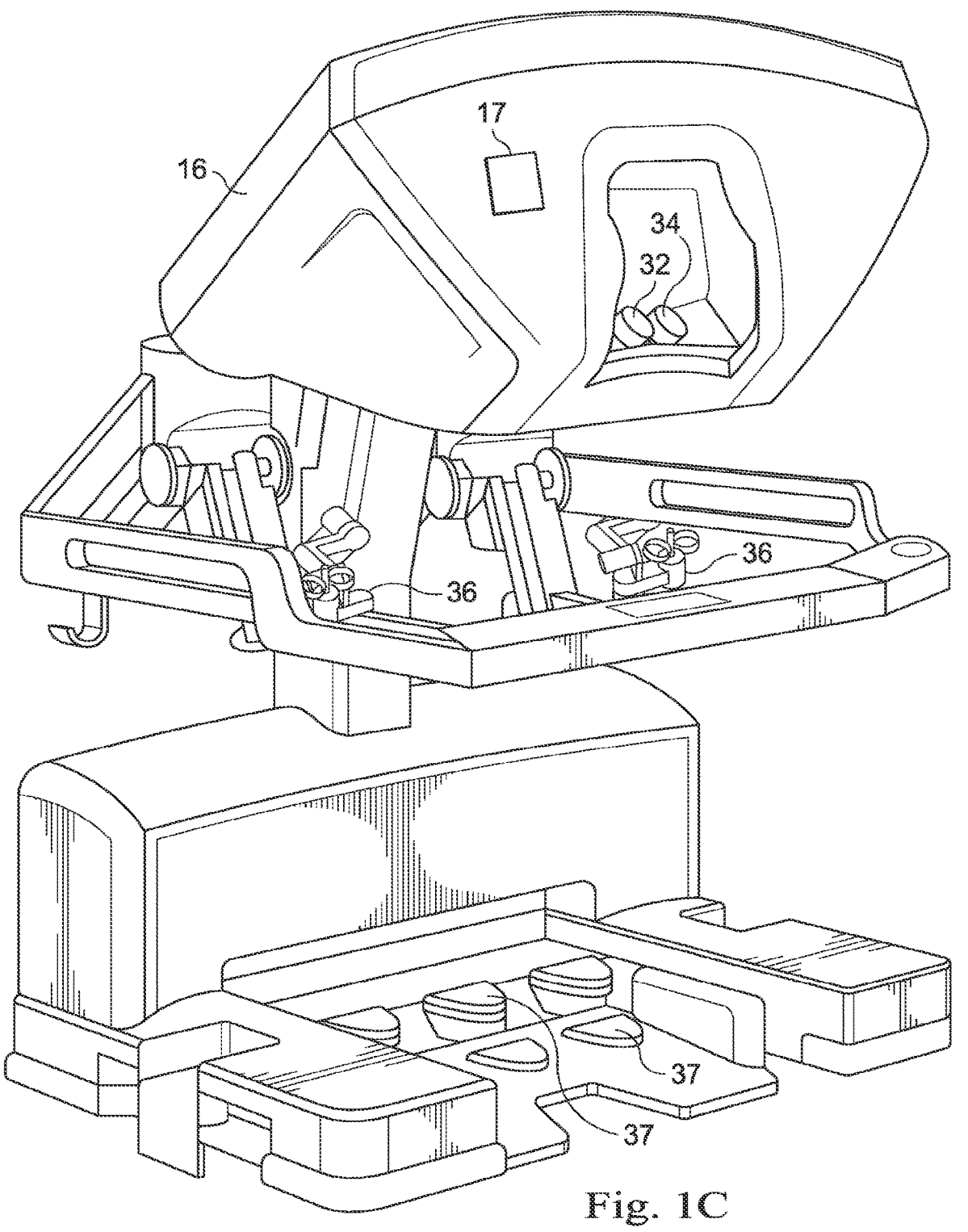
FIG. 1C is a perspective view of a surgeon's control console for a teleoperational medical system, in accordance with many embodiments.

FIG. 1C is a perspective view of the console 16. The console 16 includes a left eye display 32 and a right eye display 34 for presenting the surgeon S with a coordinated stereo view of the surgical environment that enables depth perception. The console 16 further includes one or more input control devices 36, which in turn cause the teleoperational assembly 12 to manipulate one or more instruments or the endoscopic imaging system. The input control devices 36 can provide the same degrees of freedom as their associated instruments 14 to provide the surgeon S with telepresence, or the perception that the input control devices 36 are integral with the instruments 14 so that the surgeon has a strong sense of directly controlling the instruments 14. To this end, position, force, and tactile feedback sensors (not shown) may be employed to transmit position, force, and tactile sensations from the instruments 14 back to the surgeon's hands through the input control devices 36. Input control devices 37 are foot pedals that receive input from a user's foot.

Many aspects of the console 16, the teleoperational assembly 12, and the auxiliary systems 26 are adjustable and customizable to meet the physical needs, skill level, or preferences of the surgeon S. Configuring the systems to match the surgeon's needs, skill set, and preferences can be time consuming if it has to be performed for each surgical procedure. Furthermore, surgeons may be unaware of new features of the systems or procedural efficiencies developed by other practitioners. Consequently, some clinicians accept suboptimal ergonomic conditions or fail to recognize possible procedural efficiencies when performing procedures.

As described in detail below, a user profile may be created for each user of the teleoperational system 10 to store a variety of personalized data including identification information, training history, credentials, procedure history, communication preferences, ergonomic preferences, equipment preferences, and interface preferences. The profile may be accessed before, during, and after each simulator, training, or actual surgical procedure conducted by the surgeon to configure the surgical environment, equipment, user interface, and communications to the user.

Figure 2:
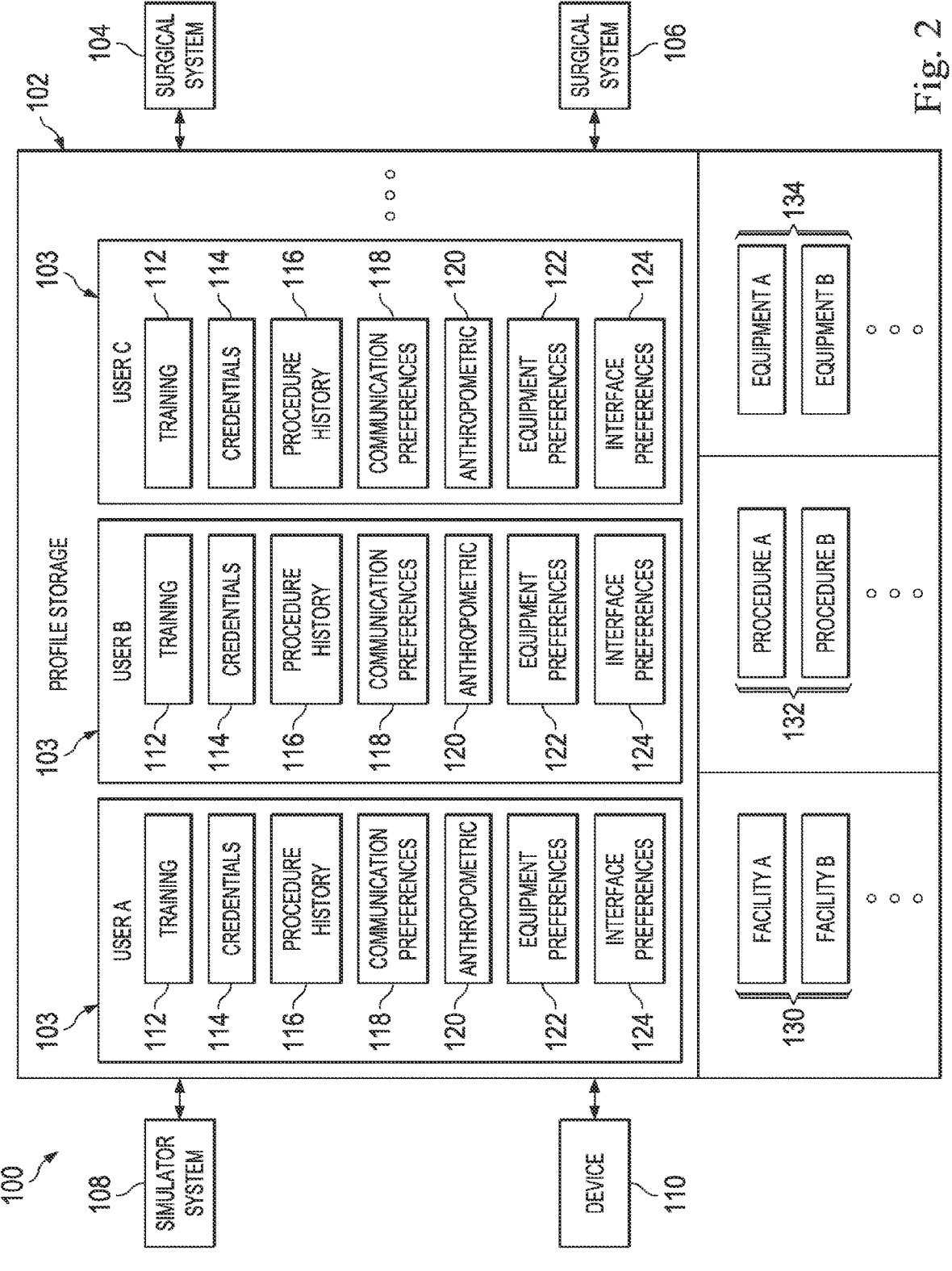
FIG. 2 is a system for maintaining a user profile.

FIG. 2 illustrates a system 100 for maintaining a user profile. The system 100 includes a profile database 102 (e.g., database 27) in communication with multiple systems and devices including, for example, a teleoperational surgical system 104 (e.g., system 10), a teleoperational surgical system 106, a simulator system 108, and a data input device 110 including, for example, a mobile phone, smart phone, tablet computer, laptop computer, wearable mobile device, desktop computer, pager, electronic badge, or other similar user devices that may passively or actively receive information from or about the user. One or more of the systems 104, 106, 108 or the device 110 may be omitted from the system. Alternatively, the profile database may be in communication with may more systems and devices than those shown in FIG. 2. For example, the profile database may reside on a server of a teleoperation system manufacturer and may be in communication with thousands of the manufacturers teleoperational systems distributed across the world. As previously described, the profile database 102 may be accessible to one or more of systems or devices 104, 106, 108, 110 via one or more networks. The one or more networks may include any suitable combination of cable, cellular, radio, digital subscriber line, or any other suitable network, which may be wired and/or wireless. In some examples, network communication may be conducted over a wireless medium, e.g., using Bluetooth, IrDA, HomeRF, IEEE 802.11, DECT, Wireless Telemetry or other protocols for wireless data communication. The profile database 102 may include records, tables, arrays, and the like, which may be relational or non-relational.

The simulator system 108 may be provided to a surgeon or other operator of a teleoperational system to create an environment in which to practice a given operation to develop facility with the system and to validate the selected entry port locations. Generally, the simulator system may include teleoperational control mechanisms, a computer with a monitor, and computer software to enable the simulation. Using a simulation, a surgeon can essentially perform the operation as it would be performed on a live patient, as simulated on a 3-dimensional representation on a computer monitor.

The profile database 102 include a user record 103 (also called profile 103) for each of a plurality of users of the systems and devices 104, 106, 108, 110. The record 103 for each user may include a training record 112, a credential record 114, a procedure history record 116, a communication preference record 118, an anthropometric record 120, an equipment preference record 122, and an interface preference record 124. Additional or alternative types of user-specific records may also be stored for some or all of the users.

The training record 112 may include, for example, a cumulative record of the user's simulator experience and proctor-assisted procedure experience, including the types of procedures, the outcome of the procedures, and any issues occurring during the procedures. It may also include evaluations, certifications, and a cumulative log of hours in training. The training record 112 may be updated after each training episode for a user. For example, after conducting a simulation exercise with simulator system 108, the simulator may communicate with the training record 112 for User A and update it to reflect completion of the simulation exercise.

The credentials record 114 may include, for example, credentials or other rights to use the systems and devices 104, 106, 108, 110 or access specific procedures with those systems. Credentials may be issued by an issuing authority such as a trainer, a medical facility (e.g., a hospital, clinic, training center). For example, if User A is authorized by a hospital to use an on-site teleoperational system, a computer (e.g., device 110) may be used to update the credential record 114 for User A. The credential record 114 may be used to limit the access of the user to any of the systems or devices 104, 106, 108, 110. For example a user who is a systems engineer and not a surgeon may have credentials that allows limited access to system 104 controls (e.g., controlling a display screen brightness) but restricts access to other functions (e.g., manipulation of the surgical instruments when a patient is present). The credential record may limit user access to procedures, instruments, and functions of the system 104 if the proper credential is not found in the credential record 114.

The procedure record 116 may include experience statistics including a count of procedures performed, types of procedures performed, speed of procedures performed, and transition times for prior procedures. The record 116 may further include the software version and model of the system used for each procedure. As described below, data from a user's procedure record may be compared with current software, equipment model, or procedure information to provide assistance or warnings to the user about differences or changes that may distinguish the current procedure from prior procedures. The procedure record 116 may be updated during and/or after each procedure conducted by User A via, for example, communication with the surgical system on which the procedure was performed The communication preferences record 118 may include a record of the languages in which the user is fluent and preferred languages for audio and/or textual communication. The communication record may also include User A's preferences regarding the medium for delivery of communication (e.g., visual, auditory, combined visual and auditory); volume settings; and preferred frequency of reminders and warnings. The communication preferences record 118 may be updated, for example, by User A using a smart phone (e.g., device 110) application that accesses the record. Alternatively, the record 118 may be updated to record the most recent communications selections during a procedure as the default communication settings for the next procedure.

The anthropometric record 120 may include anatomic measurements taken for User A including, for example, optometric measurements of User A's vision and any needed corrective lenses, intraocular spacing, height, weight, handedness, and physical limitations. The information from the anthropometric record 120 may be used to optimize the ergonomic configuration of the surgeon console viewer, including the eye displays 32, 34. For example, the anthropometric record information may be used to configure viewer height and viewer angle. The anthropometric record 120 may also include, for example, the distance between a user's elbows and eyes for determining the distance between the armrest of the surgeon console and the eye displays (e.g., the arm rest heights). The anthropometric record 120 may also include, for example, the length of a user's forearm for determining a centered neutral position for the master controls. The anthropometric record 120 may also include, for example, the length of the user's legs from hip flexor to knees for determining the position of the foot pedal tray. The anthropometric record 120 may be updated by data entry through a computer (e.g., device 110). Additionally or alternatively, a system 104, 106, 108 may include measurement devices to capture the anthropometric data while the user is engaged with the system.

The equipment preferences record 122 may include User A's preferences regarding optional arrangements, functions, and settings of components of a teleoperational system (e.g., system 10, 104, 106). The record 122 may include some user preferences and settings that pertain to specific types of assemblies 12 and some user preferences and settings that persist for any type of assembly 12. For example, the record 122 may include preferred hand positions and button/pedal function assignments for the control console 16. The record 122 may include the User A's preferred configuration of the assembly 12 relative to the patient. The record 122 may include preferred instrument (e.g., instrument 14) settings such as electrocautery power levels, coagulation/cut energy levels, force, torque, staple cartridge, and handedness for stapler. The record 122 may include preferred tele-operation associations between master controls and the controlled manipulator and/or instrument. The record 122 may include a preferred arrangement of the endoscope and instrument types on each of the manipulator arms. The record 122 may also include dominant and non-dominant hand assignments, such as the auxiliary instrument arm preference for the left or right side. The record 122 may include preferred port placements and arm configurations. The record 122 may include preferred functionality such as table motion or microsurgery capability. For example, preferred preset table positions (e.g., trendelenburg and tilt angles) may be stored for different phases of the procedure. The record 122 may include preferences regarding auxiliary equipment (e.g., auxiliary system 26) including supplemental imaging systems (e.g., MRI, x-ray, ultrasound); video input and output; carbon dioxide settings; insufflation pressure and flow rate preferences based on patient condition and phase of the procedure; and audio settings (e.g., which microphones activated, feedback suppression, which speakers activated, use of voice prompts). The record 122 may be updated to record the most recent equipment settings during a procedure as the default communication settings for the next procedure or may default to the most frequently used settings.

The user interface record 124 may include User A's preferences regarding the graphical user interface, other sensory displays, or the endoscopic instrument settings. For example, the record 124 may include preferences regarding vision correction and autofocus. The record 124 may also include User A preferences for display color, brightness, contrast, shadow, dynamic contrast, color tone, and use of near infrared imaging. The record 124 may also include User A's preferences regarding image processing enhancements for specular reflection removal, smoke removal, and noise suppression. The record 124 may also include User A's preferences regarding thresholds and filters for fluorescence imaging, segmentation, and interpretation. The record 124 may also include User A's preferences regarding the information visible to User A at the control console 16 and the arrangement of the information in tiles or other configurations on the display. The record 124 may also include User A's preferences regarding graphical overlays on the endoscopic image, including the opacity of the graphical overlays.

The profile database 102 may also include facility records 130 that include information about each facility housing surgical systems (e.g., 10, 104, 106). The record 130 may include, for example, the availability or scheduling of local systems, credential requirements for the facility, training requirements for the facility, and auxiliary equipment available at the facility. The facility record 130 may be used together with the user record 103 to configure a surgical system at the facility. For example, a Facility A at which a surgical system 104 is located, may include a record 130 requiring an authorization credential. The User A credential record 114 must include the authorization credential or the User A will be denied access to the system 104 and any other systems at Facility A.

The profile database 102 may also include procedure records 132 that include information about various procedures that may be performed with the teleoperational systems. Each procedure record 132 may include, for example, the current procedure sequence, best-practices for performing the procedure, instruments needed to perform the procedure, and the training level required to perform the procedure. The procedure sequence, best practices, and needed instruments may be predetermined by an administrator, instructor, or other authority. Alternatively, these records may be recorded from a prior teleoperational procedure. The procedure record 132 may be used together with the user record 103 to prepare for a procedure. For example, if the best practices for performing procedure A from record 132 have changed since the last time the User A performed the type of procedure A, (as recorded in the User A procedure history record 116), a visual or auditory message explaining the differences may be provided to the User A before commencing the current procedure A.

The profile database 102 may also include equipment records 134 that include information about equipment of the surgical systems (e.g., 10, 104, 106). Each record 134 may include, for example, software revision information and functional capability for the control console, control system, teleoperational assemblies, auxiliary equipment, and surgical instruments. The equipment record 134 may be used together with the user record 103 to prepare for a surgical system for use. For example, if the record 134 indicates that the current software running on system 104 is a newer revision compared to the last time User A used the system, a visual or auditory message explaining the differences may be provided to User A before commencing use of the system 104.

Figure 3:
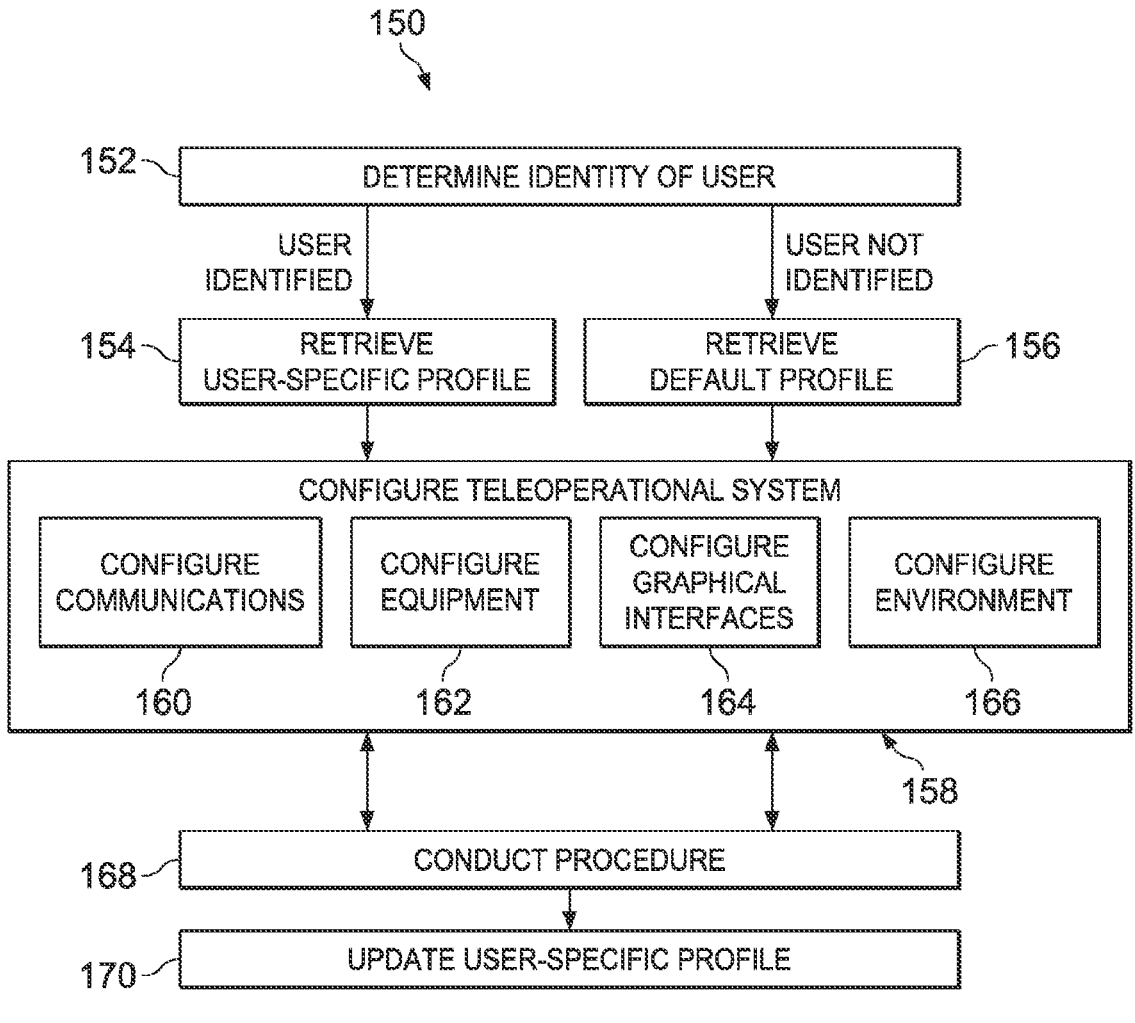
FIG. 3 is a method for conducting a teleoperational medical procedure using retrieved profiles.

Referring now to FIG. 3, a method 150 for conducting a teleoperational medical procedure using retrieved user profiles is illustrated. At a process 152, a potential user of a teleoperational medical system (e.g., a system 10) is detected and identified. For example, the control console 16 may include an identity detection system 17 for detecting identifying information about a user. The identity detection system 17 may include a head-in console iris or retinal scan recognition system, a fingerprint recognition system, a voice recognition system, a facial recognition system or other physiologic recognition system. Alternatively, the identity detection system may be based on a user-assigned identification badge using, for example radio frequency identification (RFID), magnetic strip, bar code, proximity care, or contact card technology. In various alternatives, the identity detection system, using any of the above described technologies, may begin identity detection when one or more users enter a predetermined area such as the operating room. After detecting one or more identifying characteristics, the characteristics may be compared to information from the user profiles from the profile database 102. For example, the collected identifying characteristics may be compared to anthropometric records 120 and/or credential records 114. In one example, anthropometric record 120 may include retinal measurements for User A. If those retinal measurements match detected retinal measurements from the identity detection system 17, the identity of the user is determined to be User A. In another example, credential records 114 may include RFID data associated with User A. If RFID data gathered from the identity detection system 17 matches the RFID data for an authorized User A, User A is identified as an authorized user.

At a process 154, if the identity of the user is determined, the user profile from the profile database 102 is retrieved. At a process 156, a default profile may be retrieved if the identity of the user may not be determined. Optionally, if the identity of the user is not determined, no profile is retrieved and the user is unable to use the teleoperational system 10. Alternatively, if the identity of the user is not determined, the identity may be verified manually by authorized administrative personnel with alerts provided to indicate that a non-credentialed user was operating at the console for a recorded period of time.

At a process 158, the teleoperational system 10 is configured based upon the personal profile of the identified user. For example, if User A is identified as the user, the records of profile 103 are used to configure the teleoperational system.

At a process 160, communications to User A may be configured. For example, pop-up messages, warnings, or other indications may be provided to User A based on information from the procedure history record 116. In various examples, the a message may alert User A that the system is running a software revision that includes additional features added since the last time User A conducted the same procedure, that a feature that they regularly use for the procedure is not available, or that (in combination with records 132) the user may be interested in trying a new feature or procedure sequence to improve efficiency or safety. Communications may also be configured based on a detected emotional state of the user (e.g., using iris detection, measured changes in body temperature, measure changes in perspiration). In another example, messaging may also be based upon training record 112 and may include providing a pop-up recommendation that User A use a proctor or trainer for the procedure. In another example, messaging may be provided to suggest body repositioning to allow User A to better view the full display.

Aspects of the user messaging such as the language, location, duration, and volume (if an audio or video message) may be determined by the communication records 118 of the profile 103. The provided messages may be acknowledged and cleared using any of a variety of techniques including clicking an acknowledgement on the user interface, tracking user's eye gaze to ensure that the message was read, providing a test or other comprehension evaluation, or requiring the user to perform an activity such as trying a new feature of the system. After the user has completed the requisite acknowledgement, the message may be omitted for subsequent procedures or may be provided only a limited number of subsequent times. Similarly, if the user's procedure history indicates that the user has acquired a threshold level of experience in a procedure the frequency of some messages (e.g., assistance messages or warnings) may be reduced or eliminated.

At a process 162, the equipment of the teleoperational system 10 may be configured based, for example, on the equipment preferences record 122, anthropometric record 120, training record 112, credential record 114, and/or procedural history record 116. For example, preferred hand positions and button/pedal function assignments may be made for the control console 16. The preferred configuration of the assembly 12 relative to the patient may be set-up. Preferred instrument settings may be set, such as ablation power levels, energy, force, torque, staple cartridge, and handedness for stapler. Other preferences including port placements, arm configurations, table motion or microsurgery capability may be implemented. Preferences regarding auxiliary equipment (e.g., auxiliary system 26) including supplemental imaging systems (e.g., MRI, x-ray, ultrasound); video input and output; carbon dioxide settings; and audio settings (e.g., which microphones activated, feedback suppression, which speakers activated, use of voice prompts) may also be implemented.

The process 162 of configuring the equipment of the teleoperational system may further include determining the type of teleoperational assembly 12 being used in the present procedure and configuring the equipment based on the type of teleoperational assembly. For example, motion scale settings may be selected based a user record that applies different motion scale settings depending on the type of teleoperational assembly performing the present procedure. Some equipment configuration settings in the user profile may be equivalent across different teleoperational platforms (e.g., image brightness, speaker volume), but other settings of the user profile that are inherently distinct to interactions with particular platforms may be persisted separately.

At a process 164, the user interface, including the graphical user interface visible on the display of the console 16, is configured based, for example on the interface preference record 124, the anthropometric record 120, the training record 112, the credential record 114, and/or the procedural history record 116. For example, vision correction and autofocus preferences may be configured by adjustments on the console 16 or the endoscopic system 15. Adjustments for display color, brightness, contrast, shadow, dynamic contrast, and use of near infrared imaging may be made. User A's preferences regarding the information visible to User A at the control console 16 and the arrangement of the information in tiles or other configurations on the display may also be implemented. User A's preferences regarding graphical overlays on the endoscopic image, including the opacity of the graphical overlays may also be implemented.

At a process 166, other adjustable aspects of the user environment may be configured based upon the records for the profile 103. If at process 156, a default profile was retrieved, a default or test set-up configuration of the communications system, equipment, and user interfaces may be implemented. Optionally, some of the default settings may be adjusted by the unidentified user.

At a process 168, User A conducts the teleoperational medical procedure using the configurations based upon the user profile 103. Throughout the procedure, communications, equipment, user interfaces, and other aspects of the user's environment may be controlled by the user profile 103.

At a process 170, if User A makes configuration changes that differ from preferences stored in the records of the profile 103, the system may update the profile or may query the user to determine whether the user would like the changed configurations to replace (either entirely or contextually) preferences stored in the records of the profile. The user profile is also accessible outside of the surgical environment so that a user can import, export, and modify parameters of the profile. Profiles may also be created, deleted, and populated by an administrator. An administrator may also populate the profile with procedures for which the user has been credentialed to perform.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
a teleoperational assembly including an operator input system and a teleoperational manipulator configured for operation by the operator input system, wherein the teleoperational manipulator is coupled to a medical instrument in a surgical environment; and
a processing unit including one or more processors, wherein the processing unit is configured to:
retrieve a user profile for a user, the user profile including a parameter established during a prior teleoperational procedure, wherein the parameter includes an ergonomic setup for an input device of the operator input system, the input device configured to operate the teleoperational manipulator;
capture anthropometric data for the user when the user is engaged with the operator input system;
provide instructions to configure an operation of the teleoperational assembly based upon the parameter and to optimize an ergonomic configuration of the operator input system based upon the captured anthropometric data for the user, wherein the operation includes adjusting the operator input system based on at least the ergonomic setup for the input device of the operator input system and the optimized ergonomic configuration of the operator input system; and
based on the instructions, manipulate, via the teleoperational manipulator, the medical instrument in the surgical environment in response to signals received from the input device.

2. The system of claim 1, wherein the processing unit is further configured to determine an identity of the user, wherein the user profile is associated with the identity.

3. The system of claim 2, wherein determining the identity of the user includes receiving biometric information about the user.

4. The system of claim 1, wherein retrieving the user profile includes retrieving the user profile over a network from a profile storage database.

5. The system of claim 1, wherein the parameter further includes a procedural sequence of the prior teleoperational procedure.

6. The system of claim 5, wherein the operation further includes providing a message to the user based on the procedural sequence.

7. The system of claim 6, wherein the processing unit is further configured to clear the message based on an indication of an activity completed by the user.

8. The system of claim 5, wherein the operation further includes adjusting a setting of the operator input system based on the procedural sequence of the prior teleoperational procedure.

9. The system of claim 1, wherein the operation further includes adjusting the operator input system based on the anthropometric data.

10. The system of claim 1, wherein the operation further includes adjusting an operating table based on the anthropometric data.

11. The system of claim 1 wherein the parameter further includes a credential issued to the user based on the prior teleoperational procedure.

12. The system of claim 1 wherein the parameter further includes a setting for the medical instrument based on a user preference established during the prior teleoperational procedure.

13. The system of claim 1 wherein the parameter further includes a setting for auxiliary equipment.

14. The system of claim 1, wherein the parameter further includes at least one of an ergonomic setup for the operator input system, a vision correction setting, a preferred language setting, or a preferred graphical user interface setting.

15. The system of claim 1, wherein the prior teleoperational procedure was conducted by the user.

16. The system of claim 1, wherein the prior teleoperational procedure was conducted by another user.

17. The system of claim 1, wherein the prior teleoperational procedure was a simulated teleoperational procedure.

18. The system of claim 1, wherein the processing unit is further configured to determine a type of the teleoperational manipulator and wherein providing instructions to configure an operation of the teleoperational assembly is further based on the type of the teleoperational manipulator.

19. The system of claim 18, wherein the type is a single port teleoperational manipulator or a multi-port teleoperational manipulator.

20. The system of claim 1, wherein the anthropometric data comprises optometric measurements for the user.

* * * * *